US010081461B2

(12) United States Patent
Herbelin

(10) Patent No.: US 10,081,461 B2
(45) Date of Patent: Sep. 25, 2018

(54) DEVICE FOR DISPENSING POWDER, CAP FOR SUCH A DEVICE AND WORKSTATION COMPRISING SUCH A DEVICE

(71) Applicant: XPERT AUTOMATION, Pommeuse (FR)

(72) Inventor: Patrick Herbelin, Pommeuse (FR)

(73) Assignee: XPERT AUTOMATION, Pommeuse (FR)

( * ) Notice: Subject to any disclaimer, the term of this patent is extended or adjusted under 35 U.S.C. 154(b) by 1163 days.

(21) Appl. No.: 14/358,293

(22) PCT Filed: Nov. 23, 2012

(86) PCT No.: PCT/EP2012/073512
§ 371 (c)(1),
(2) Date: May 15, 2014

(87) PCT Pub. No.: WO2013/079415
PCT Pub. Date: Jun. 6, 2013

(65) Prior Publication Data
US 2014/0311088 A1    Oct. 23, 2014

(30) Foreign Application Priority Data
Nov. 30, 2011 (FR) ..................... 11 60985

(51) Int. Cl.
*G01F 11/00* (2006.01)
*B65D 47/06* (2006.01)
(Continued)

(52) U.S. Cl.
CPC ........... *B65D 47/06* (2013.01); *G01F 23/205* (2013.01); *G01G 13/003* (2013.01); *G01G 13/02* (2013.01);
(Continued)

(58) Field of Classification Search
CPC .................. B65D 47/06; G01G 13/24
(Continued)

(56) References Cited

U.S. PATENT DOCUMENTS 5,392,648 A * 2/1995 Robertson ................. G01F 3/16
222/59
2005/0242117 A1* 11/2005 Yoshida ................ G01F 23/292
222/113

(Continued)

FOREIGN PATENT DOCUMENTS

EP    2 369 311 A1    9/2011
FR    2 846 632 A1    5/2004

OTHER PUBLICATIONS

International Search Report for PCT/EP2012/073512 dated May 17, 2013.

*Primary Examiner* — Jeremy W Carroll
(74) *Attorney, Agent, or Firm* — Sughrue Mion, PLLC

(57) ABSTRACT

The invention relates to a device for dispensing powder, comprising at least one storage tank (1) provided with a cap (2) comprising a flow orifice (3) for the powder. According to the invention, the device comprises a shutter (8) provided with an aperture (9) and fitted so as to be able to move relative to the cap between a shut position preventing the powder from flowing and an open position allowing the powder to flow through the aperture of the shutter, a channel (12) passing through the shutter so as to extend on either side of the aperture of the shutter in a direction that is substantially transverse to the flow of the powder, and means for creating a relative motion between the cap and the shutter in order to move the shutter between its two positions, said means being connected to a control unit (20) that is connected to contactless means for detecting the flow of the powder, the detecting means comprising, at a first end of the channel of the shutter, at least one emitter (21) emitting a (Continued)

wave into the channel and, at a second end of the channel, at least one receiver (22) for detecting the emitted wave. The invention also relates to a workstation comprising such a device for dispensing powder.

26 Claims, 7 Drawing Sheets

(51) Int. Cl.
*G01G 13/00* (2006.01)
*G01F 23/20* (2006.01)
*G01G 13/02* (2006.01)
*G01G 13/24* (2006.01)
*G01N 35/00* (2006.01)

(52) U.S. Cl.
CPC ... *G01G 13/24* (2013.01); *G01N 2035/00217* (2013.01)

(58) Field of Classification Search
USPC .......................................................... 222/409
See application file for complete search history.

(56) References Cited

U.S. PATENT DOCUMENTS

| | | | |
|---|---|---|---|
| 2006/0011653 A1* | 1/2006 | Fontaine | G01G 13/024 222/181.1 |
| 2008/0035666 A1* | 2/2008 | Porras | H01L 21/6715 222/1 |
| 2008/0169043 A1* | 7/2008 | Osborne | A61J 1/20 141/1 |

* cited by examiner

Zoom

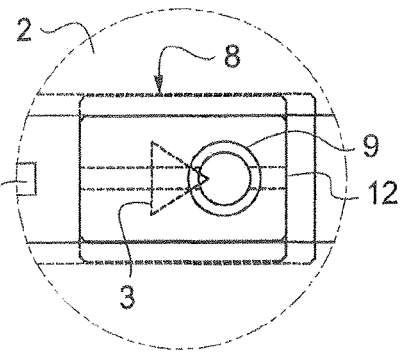
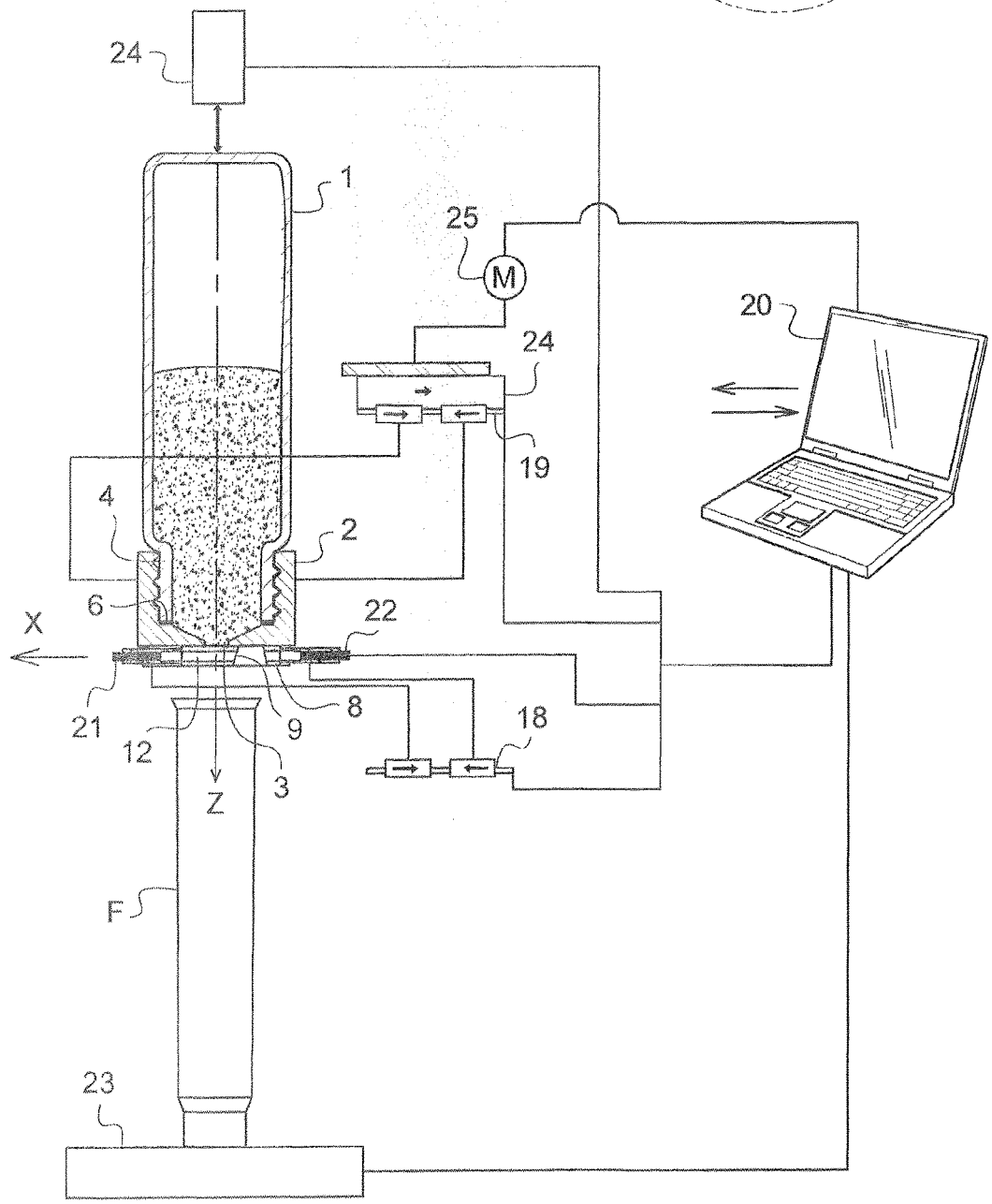

DEVICE FOR DISPENSING POWDER, CAP FOR SUCH A DEVICE AND WORKSTATION COMPRISING SUCH A DEVICE

CROSS REFERENCE TO RELATED APPLICATIONS

This application is a National Stage of International Application No. PCT/EP2012/073512 filed Nov. 23, 2012, claiming priority based on French Patent Application No. 1160985, filed Nov. 30, 2011, the contents of all of which are incorporated herein by reference in their entirety.

The invention relates to a device for dispensing powder, cap for such a device and workstation comprising such a device.

TECHNOLOGICAL BACKGROUND OF THE INVENTION

In the chemical and pharmaceutical industry, it is often necessary to produce extremely precise doses of reagents or products in the form of a powder. This is the case, for example, in laboratories in which molecules are tested or compositions are processed by mixing products. Those products are taken from libraries of samples in which the samples are conserved in the form of small quantities of powder stored in small flasks or reservoirs. The product quantity per sample being limited, it is necessary to use only the smallest possible quantity of product in order not to bring about rapid exhaustion of the library.

Some libraries of samples are provided with an automatic powder dispensing device.

There are automatic dispensing devices which comprise a storage reservoir which is provided with a dosage cap whose opening is adjustable. In accordance with an instruction regarding the quantity of powder to be dispensed and an indication of the quantity of powder already dispensed, a control unit controls the dosage cap in order to increase or decrease the opening thereof. The indication of the quantity of powder is provided by a so-called precision balance, the resolution of such a balance being, for example, $\frac{1}{10}^{th}$ of a milligram or $\frac{1}{100}^{th}$ of a milligram.

In the document FR 2846632, the indication of the quantity of powder already dispensed is provided in the same manner by weighing means, the weighing means being arranged under a flask receiving the powder.

However, it is difficult to supply quantities of powder of a few tenths of a milligram in a precise and repetitive manner with such devices. This is because generally, when a balance indicates a first mass value of dispensed powder, the quantity of powder dispensed already exceeds the initial instruction. In fact, the balance detects the start of flow of the powder into the flask at the time the powder touches the bottom of the flask, introducing an excessively large discrepancy for the dispensing of very small quantities of powder, even if the balance has a very high level of precision.

OBJECT OF THE INVENTION

An object of the invention is to provide a means which ensures more precise detection of the start of the flow of the powder than the devices of the prior art.

BRIEF STATEMENT OF INVENTION

In order to achieve this object, there is proposed a powder dispensing device which comprises at least one storage reservoir which is provided with a cap comprising a flow hole for the powder.

According to the invention, the device comprises:
a closure member which is provided with an opening and which is mounted so as to be movable relative to the cap between a closed position which prevents a flow of the powder and an open position which allows the flow of the powder through the opening of the closure member, a bore extending through the closure member so as to extend at one side and the other of the opening of the closure member in a direction which is substantially transverse relative to the flow of the powder;
relative displacement means of the cap and the closure member in order to move the closure member into the two positions thereof, those means being connected to a control unit which is connected to contactless detection means of the flow of the powder, the detection means comprising, at a first end of the bore of the closure member, at least one transmitter of a wave in the bore and, at a second end of the bore, at least one receiver for detecting the wave transmitted.

In this manner, the detection of the flow of the powder is ensured downstream of the flow hole substantially in the region of the hole which ensures very precise detection of the flow of the powder towards, for example, a flask to be filled and in particular very precise detection of the start of the flow.

The inventor has thus been able to develop a prototype which detects the start of the flow of the powder with a time interval of approximately 50 microseconds. With a device of the prior art comprising weighing means, if the balance is arranged at a distance of 45 millimeters from the reservoir, the balance detects the start of the flow with a discrepancy which may be up to 100 milliseconds in relation to the device of the invention.

The device of the invention thereby allows quantities of powder to be supplied in the order of a few tenths of a milligram in accordance with the fineness of the powder and the density of the product.

In an advantageous manner, the wave transmitted interacts directly with the powder when the powder flows through the opening of the closure member. The detection of the start of the flow is further very precise.

According to the invention, there is also proposed a cap for such a device and a workstation comprising such a device.

BRIEF DESCRIPTION OF THE DRAWINGS

The invention will be better understood in light of the following description of non-limiting embodiments of the invention. Reference will be made to the appended FIGURES, in which:

FIG. 6 is a schematic bottom view of the closure member and the cap in a construction variant of the invention;

FIG. 7 is a view similar to FIG. 1 of a device according to a second embodiment;

DETAILED DESCRIPTION OF THE INVENTION

Figure 1:
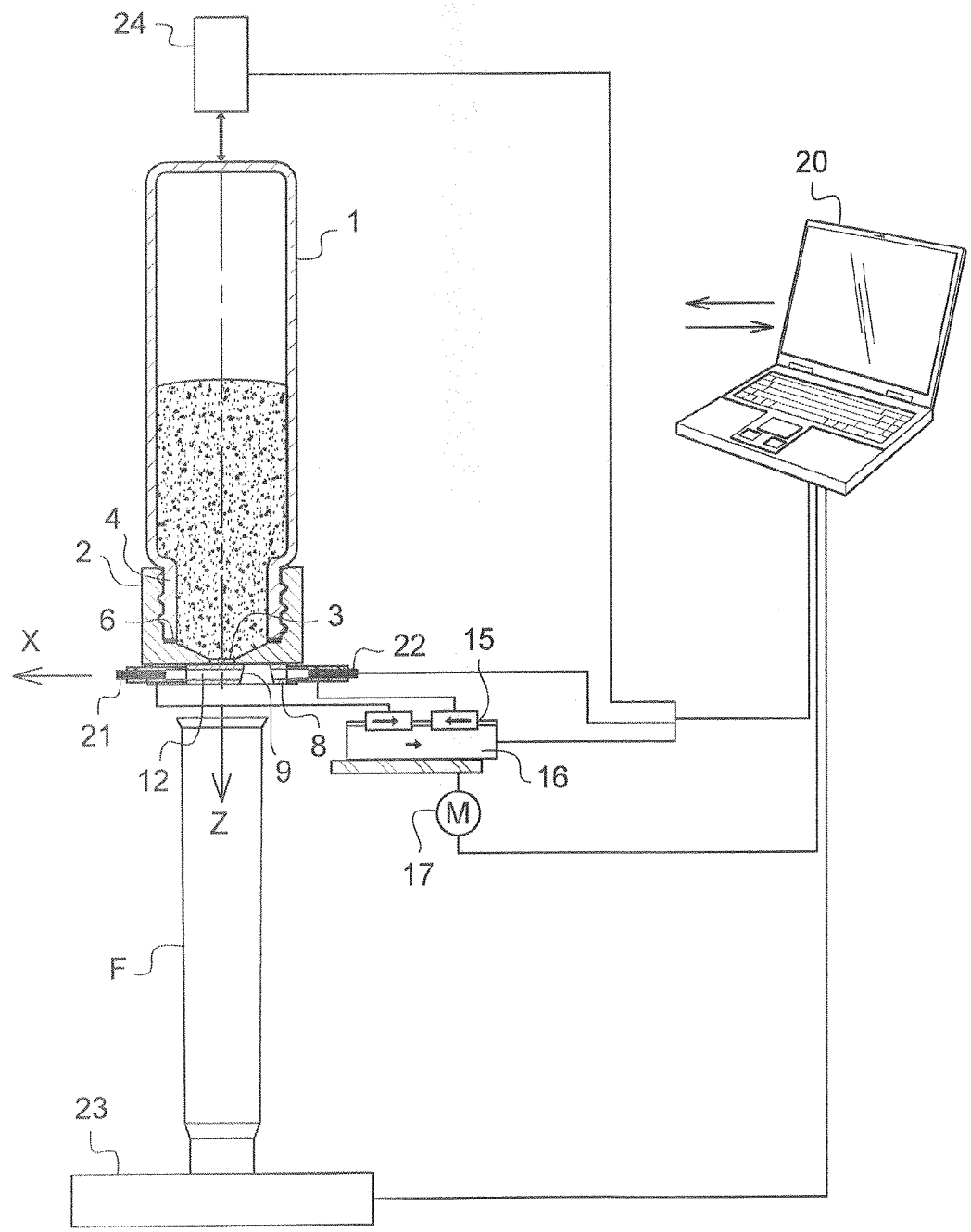
FIG. 1 is a schematic view of the powder dispensing device according to a first embodiment of the invention.

With reference to FIG. 1, the powder dispensing device according to the first embodiment of the invention comprises a storage reservoir 1 of the powder. The storage reservoir 1 is provided with a cap 2 which comprises a flow hole 3 for the powder. The reservoir 1 is, for example, a glass vial having a capacity of 4 milliliters.

During operation, the reservoir 1 is arranged in such a manner that a flow of the powder towards the outer side of the reservoir is brought about by gravitational force. The reservoir is in this instance arranged vertically, with the cap at the bottom, so that the powder then flows in a flow direction having a first substantially vertical axis Z.

According to a specific embodiment, the reservoir 1 comprises a neck 4 of which one external surface is threaded.

Figure 3A:
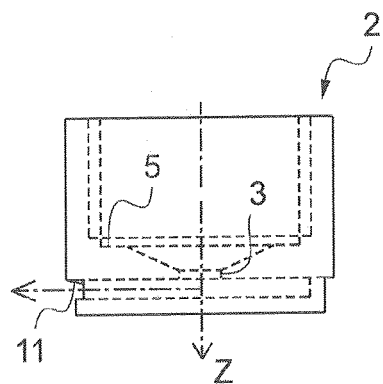
FIGS. 3a and 3b are respectively a front view and a side view of a cap of the device illustrated in FIG. 1.
Figure 3B:
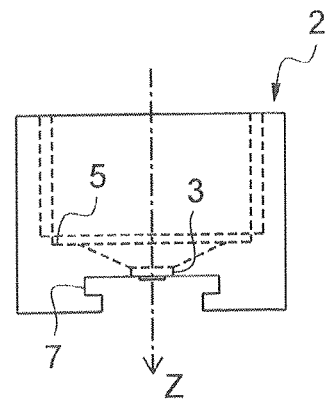

Preferably, with reference to FIGS. 3a and 3b, the cap 2 comprises a tubular wall which has cylindrical internal and external surfaces having a centre axis parallel with the first axis Z and an end closed by a partition which is pierced by the hole 3. The internal surface of the cap 2 is tapped in order to allow the engagement thereof with the neck 4. The partition has an external perimeter forming a shoulder 5 which is capable of receiving a sealing washer 6 which is intended to be clamped between the neck 4 and the shoulder 5 (as can be seen more clearly in FIG. 1). The partition comprises, at the side of the reservoir 1, a frustoconical surface portion which extends from the shoulder 5 as far as the hole 3 in order to make it easier for the powder to flow towards the flow hole 3 which has a circular contour in this instance.

According to a preferred embodiment, a face of the partition comprising the flow hole 3 comprises, opposite the reservoir, a groove 7 which extends substantially in accordance with a second axis X which is orthogonal to the first axis Z, the groove 7 being arranged in the face of the partition in such a manner that the flow hole 3 opens in the groove 7. Preferably, the groove 7 is arranged in the face in such a manner that the flow hole 3 is centered in the groove 7. Here, the groove 7 is arranged in the face of the partition so as to extend substantially at the centre of the face.

According to the invention, with reference to FIG. 1, the device comprises a closure member 8 mounted on the cap 2.

Figure 2A:
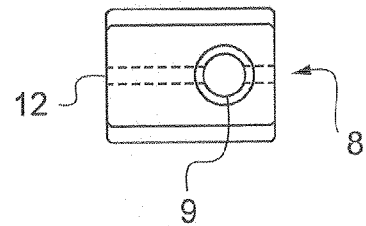
FIGS. 2a and 2b are respectively a view from below and a side view of a closure member of the device illustrated in FIG. 1.
Figure 2B:
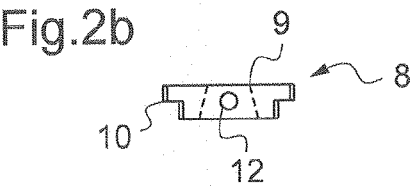

With reference to FIGS. 2a and 2b, the closure member 8 comprises an opening 9 which extends through the closure member 8 substantially in a direction parallel with the first axis Z.

Furthermore, the closure member 8 has opposite edges 10 which are slidingly engaged in the groove 7 of the cap 2. According to a specific embodiment, the groove 7 and the edges 10 form a connection of the dovetail type.

The closure member 8 is formed so as to be mounted in a movable manner relative to the cap 2 between a closure position which prevents flow of the powder, the opening 9 of the closure member not being aligned with the flow hole 3 of the cap 2, and an open position which allows flow of the powder through the opening 9 of the closure member 8, the opening 9 of the closure member 8 being at least partially aligned with the flow hole 3 of the cap 2. According to a preferred embodiment, the opening 9 and the flow hole 3 are formed in such a manner that, in the open position, the opening 9 and the hole 3 are convergent. In the open position, the powder then flows at a maximum flow rate.

According to a preferred embodiment, as can be seen more clearly in FIGS. 2a and 2b, the groove 7 of the cap is blind at one of the ends thereof so that, in the closure position, the edges 10 move into abutment against the end of the groove 7. Preferably, the cap 2 comprises a stud 11 which is arranged in the other of the ends of the groove 7 so that, in the open position, one of the edges 10 moves into abutment against the stud 11.

Preferably, the opening 9 is formed substantially in the manner of a cone which widens from a first face of the closure member 8 which faces the cap 2 to a second face of the closure member 8 which is opposite the first face. In this manner, the powder flows more readily. That allows any risk of agglomeration of the grains of powder during passage in the opening 9 to be minimized.

Preferably, in the region of the first face of the closure member 8, the opening 9 has a circular cross-section which is identical to the flow hole 3 of the cap 2.

The closure member 8 further comprises a through-bore 12 which extends at one side and the other of the opening of the closure member 8 in a direction substantially transverse relative to the first axis Z. The direction in which the bore 12 extends thus intersects with the first axis Z when the closure member 8 is in the open position.

In a preferred manner, the bore 12 extends substantially in a closure member displacement direction between the open position and the closure position, that is to say, here a direction substantially parallel with the second axis X. In this manner, the direction in which the bore 12 extends intersects with the first axis Z substantially when the opening 9 of the closure member 8 is tangential relative to the flow hole 3.

The device further comprises relative displacement means of the cap and the closure member in order to move the closure member 8 into the closure position or into the open position. With reference to FIG. 1, the displacement means in this instance displace the closure member 8 between the closure position and the open position.

According to a specific embodiment, the displacement means comprise a set of pincers 15 having parallel jaws. Each jaw is intended to cooperate with an opposing lateral face of the closure member 8 so as to clamp the closure member 8 between the two jaws.

The displacement means also comprise in this instance a movable plate 16, on which the set of pincers 15 is arranged in such a manner that a displacement of the movable plate 16 brings about a corresponding displacement of the set of pincers 15 and thereby a displacement of the closure member 8 from the closure position to the open position (and vice versa) when the closure member 8 is clamped between the two jaws. A motor 17 allows, for example, the plate 16 to be displaced.

The displacement means are connected to a control unit 20 which in this instance controls actuation of the set of pincers 15 and a displacement of the movable plate 16.

The control unit 20 is further connected to contactless detection means for the flow of the powder. The contactless detection means in this instance comprise luminous detection means which comprise, at a first end of the bore 12 of the closure member 8, at least one transmitter 21 of a light beam into the bore 12 and, at a second end of the bore 12, at least one receiver 22 for detecting the light beam. In this manner, the light beam passes through the closure member 8 via the bore 12 and necessarily intersects with the first axis Z when the closure member 8 is in an open position.

The transmitter 21 and the receiver 22 are carried by the displacement means. Here, one of the jaws carries the transmitter 21 and the other of the jaws carries the receiver 22, the set of pincers 15 clearly being arranged in such a manner that, when the jaws clamp the closure member 8, the transmitter 21 and the receiver 22 extend at the opposite ends of the bore 12.

The device further comprises a precision balance 23 which is arranged under the storage reservoir 1 and which is also connected to the control unit 20 in order to assist in determining a quantity of powder dispensed.

The device comprises tapping and/or vibration means 24 in order to assist the flow of the powder, which means are connected to the control unit 20. Such means 24 are particularly suitable for dispensing adhesive powder or powder which has a tendency to agglomerate. Since tapping and/or vibration means 24 are well known in the prior art, they will not be described here in greater detail.

A dispensing cycle of a powder dose will now be described in accordance with a specific, non-limiting embodiment of the first embodiment of the invention.

Figure 5A:
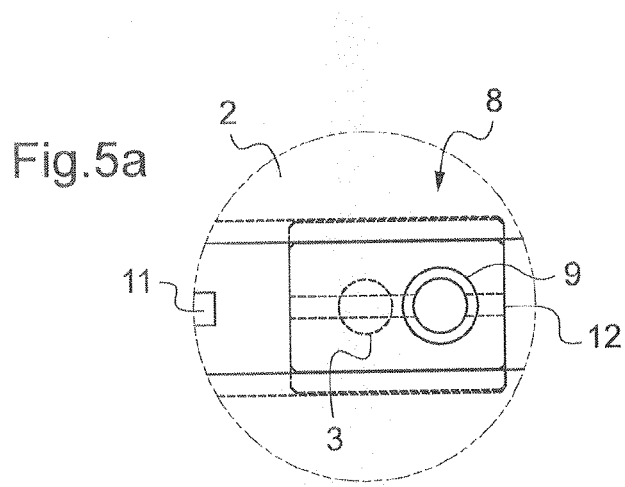
FIGS. 5a, 5b and 5c are schematic bottom views of the closure member and the cap in the course of the different dispensing steps illustrated in FIGS. 4a, 4b and 4c, respectively.
Figure 4A:
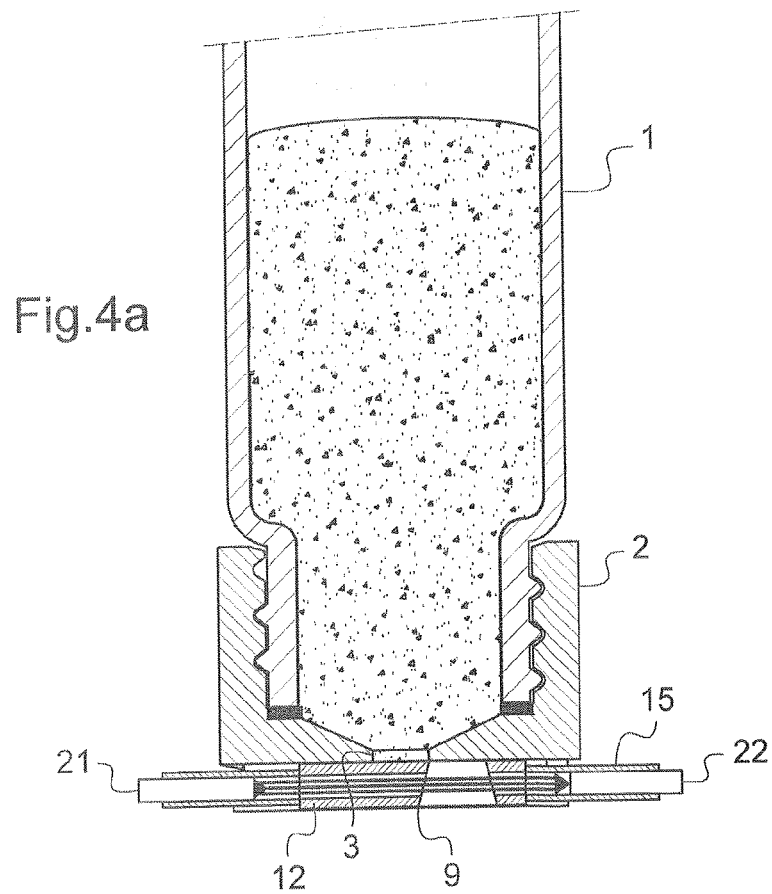
FIGS. 4a, 4b and 4c are schematic views illustrating different powder dispensing steps by means of the device illustrated in FIG. 1.

In an initial situation, a flask F is arranged on the balance 23 below the storage reservoir 1. With reference to FIGS. 4a and 5a, the closure member 8 is then in a closure position so that the light beam transmitted by the transmitter 21 is received in its entirety by the receiver 22.

Subsequently, an instruction regarding a quantity of powder to be dispensed is supplied to the control unit 20.

The control unit 20 then generates an instruction for displacing the closure member 8 and intended for the displacement means. The jaws clamp the closure member 8 then the movable plate 16 moves in order to bring about a translation of the closure member 8 from the closure position towards the open position in accordance with a first predetermined increment.

Figure 5B:
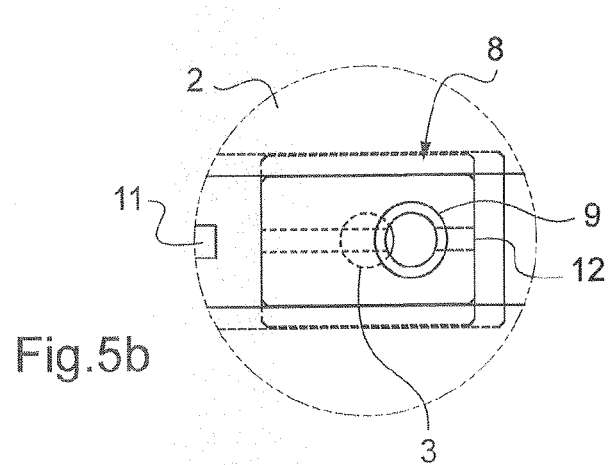
Figure 4B:
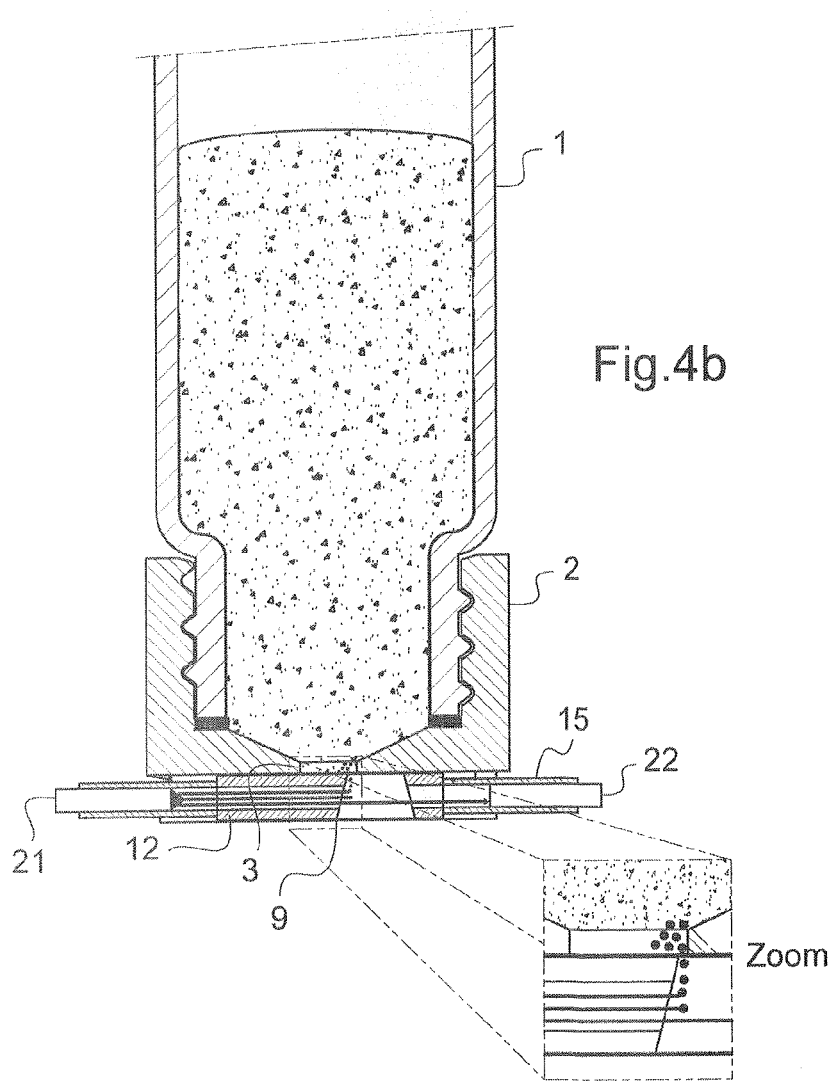

With reference to FIGS. 4b and 5b, the closure member 8 is displaced in such a manner that the opening 9 is tangent to then aligned partially with the hole 3. The first grains of powder begin to flow towards the flask F through the hole 3 and the opening 9. The light beam received by the receiver 22 is then attenuated by the grains. It should be noted that it is important that the geometry of the opening 9 and the hole 3 is such that the first grains fall into the beam.

By means of the signal which the control unit 20 receives from the luminous detection means, the control unit 20 thereby determines the start of the powder being dispensed.

In an advantageous manner, as a result of the arrangement of the bore 12, with relatively weak coincidence between the opening 9 and the hole 3, the light beam necessarily passes through the first axis Z, which ensures a very precise detection of the start of the flow.

If a start of flow of the powder is not detected after the opening of the closure member in accordance with the first increment, the control unit 20 generates an actuation instruction intended for the tapping and/or vibration means 24. If a start of flow of the powder is still not detected after a tapping action, the control unit 20 generates an instruction for displacement in accordance with a second increment.

This control procedure is carried out in an iterative manner until the start of the flow is detected. The number of increments corresponding to the position of the closure member 8 relative to the cap 2 when the start of the flow is detected is then stored and the closure member 8 is brought into a closure position. The quantity of powder supplied is then weighed by the balance 23 which generates a weighing signal intended for the control unit 20.

On the basis of the information supplied by the balance 23 and the detection means, the control unit 20 determines the conditions (position of the closure member 8 relative to the cap and/or tapping) which allow the desired dispensing of powder.

Figure 5C:
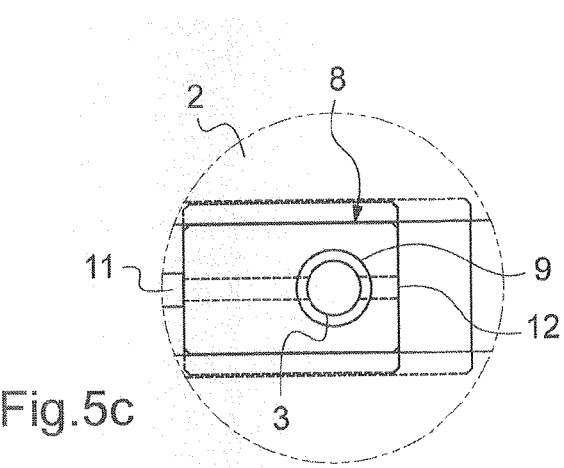
Figure 4C:
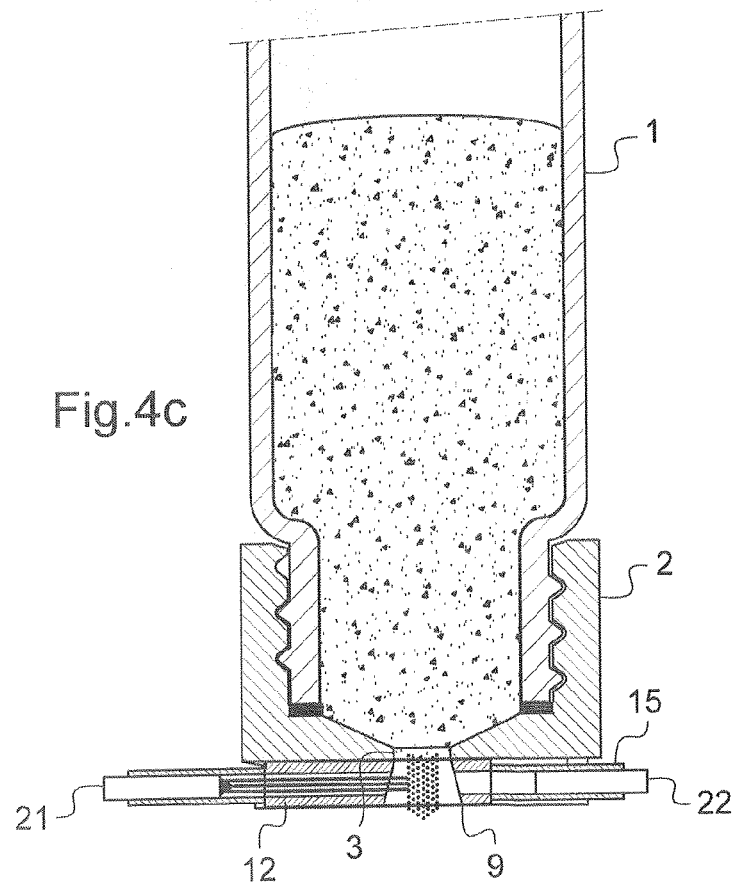

With reference to FIGS. 4c and 5c, the closure member 8 is then, for example, displaced until it reaches an open position. The flow rate of the powder is then at a maximum. A greater quantity of grains interacts with the light beam which can thereby be completely cut off, at least intermittently.

On the basis of the signal received from the balance 23, the control unit 20 derives a quantity of powder which has already been dispensed which it compares with the instruction for a quantity of powder to be dispensed.

During a final step, the control unit 20 generates an instruction for displacing the closure member and intended for the displacement means. The movable plate 16 is displaced so as to bring about a translation of the closure member 8 in order to bring the closure member 8 into the closure position.

According to a preferred embodiment, once the closure member 8 is in the closure position, the control unit 20 compares the signal provided by the balance 23 with the instruction concerning a quantity of powder to be dispensed in order to verify whether the instruction has been complied with.

In this manner, the device of the invention allows the flow of the powder to be controlled very precisely.

In an advantageous manner, the device of the invention can be adapted to any type of reservoir and in particular the reservoirs already in use in combinatorial libraries. This is because it is simply necessary to adapt the tapped portion of the cap to the reservoir desired.

With reference to FIG. 7, a second embodiment will now be described. The common elements with respect to the first embodiment illustrated in FIG. 1 retain the same numbering.

In the first embodiment, the relative displacement means of the cap and the closure member displaced the closure member 8 between the closure position and the open position.

In the second embodiment, the relative displacement means of the cap and the closure member displace in this instance the cap 2 and therefore the reservoir 1 so as to bring the closure member 8 between the closure position and the open position.

The relative displacement means of the cap and the closure member preferably comprise a first set of pincers 18 having parallel jaws, each jaw being intended to cooperate with an opposing lateral face of the closure member 8 so as to clamp the closure member 8 between the two jaws. The first set of pincers 18 thereby maintains the closure member 8 above the flask F in a given fixed position in relation to the flask F so that the opening 9 of the closure member 8 is centered relative to an open end of the flask F. As for the first embodiment, the first set of pincers 18 carries the transmitter 21 and the receiver 22. One of the jaws of the first set of pincers 18 carries the transmitter 21 and the other of the jaws carries the receiver 22, the first set of pincers 18 clearly being arranged so that, when the jaws surround the closure member 8, the transmitter 21 and the receiver 22 extend at the opposite ends of the bore 12.

The relative displacement means of the cap and the closure member further comprise a second set of pincers 19 having parallel jaws, each jaw being intended to cooperate with diametrically opposite surfaces of the cap 2 so as to clamp the cap 2 between the two jaws.

The displacement means also comprise here a movable plate 24 on which the second set of pincers 19 is arranged so that a displacement of the movable plate 24 brings about a corresponding displacement of the second set of pincers 19 and thereby a displacement of the cap 2, and therefore of the reservoir 1, in order to bring the closure member 8 from the closure position to the open position (and vice versa) when the cap 2 is clamped between the two jaws. A motor 25 allows, for example, the movable plate 24 to be displaced.

The displacement means are connected to the control unit 20 which here controls actuation of the second set of pincers 19 and a displacement of the movable plate 24.

In an advantageous manner, as a result of the second embodiment, the opening 9 of the closure member 8 remains fixed with respect to the flask F and is preferably centered about the open end of the flask F. Grains of powder are thereby prevented from becoming deposited on the rim of the open end of the flask F and those grains are prevented from falling out of the flask F when the flask F is closed, thereby corrupting the quantity of powder dispensed.

In this manner, the device of the invention allows the flow of the powder to be controlled very precisely.

Figure 8:
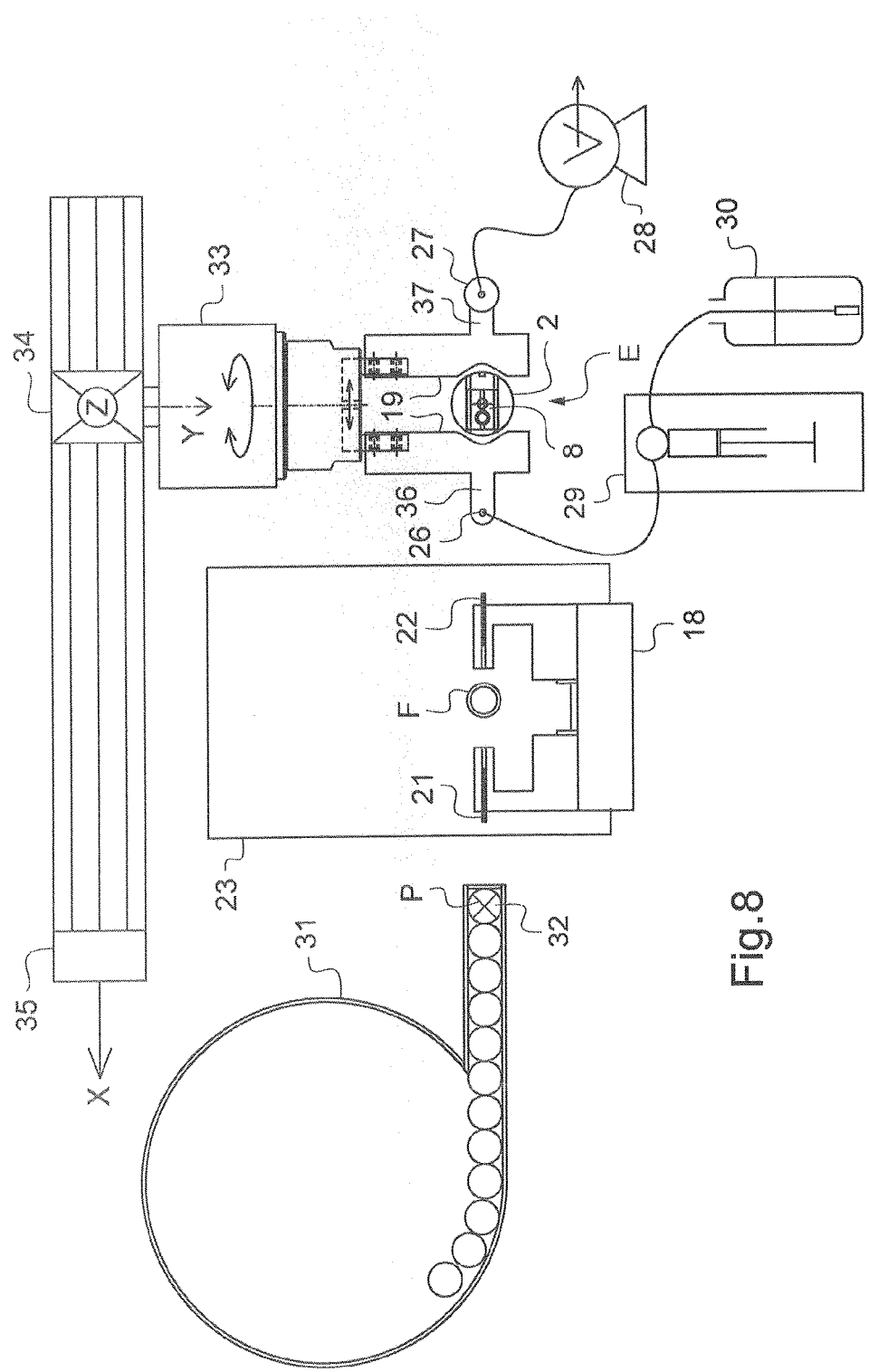
FIG. 8 is a very schematic plan view of a workstation comprising a powder dispensing device according to the second embodiment.

With reference to FIG. 8, there is described a workstation comprising a powder dispensing device according to the second embodiment. The common elements with respect to the second embodiment illustrated in FIG. 7 retain the same numbering.

The first set of pincers 18 is arranged in the workstation in order to extend above the balance 23 in a permanent manner. Except for the relative movement of one of the jaws of the first set of pincers 18 relative to the other of the jaws of the first set of pincers 18, the first set of pincers 18 has a fixed position in the workstation relative to the balance 23.

The relative displacement means of the cap and the closure member are here arranged in the workstation in order also to displace, in the workstation, an assembly E which is formed by the reservoir 1, the cap 2 and the closure member 8.

To this end, the displacement means comprise a rotation unit 33 to which the second set of pincers 19 is connected in order to allow the assembly E to rotate about a third axis Y which is orthogonal to the first axis Z and to the second axis X. The displacement means also comprise a lifting unit 34, to which the rotation unit 33 is connected in order to allow the translation of the rotation unit 33, and thereby of the assembly E, about the first axis Z. The displacement means also comprise a translation unit 35, to which the lifting unit 34 is connected in order to allow the translation of the lifting unit 34, and thereby of the assembly E, along the second axis X.

The displacement means are connected to the control unit which in this instance controls in particular actuation of the first set of pincers 18, the second set of pincers 19, the rotation unit 33, the lifting unit 34 and the translation unit 35.

In a preferred manner, the workstation further comprises a device for dispensing a solvent to the flask F in order to dispense a volume of solvent to the flask F once the desired quantity of powder has been poured into the flask F. Preferably, this volume is determined on the basis of a concentration instruction which the control unit 20 has received.

To this end, the device for dispensing a solvent comprises a container 30 which comprises the solvent to be dispensed and means for dispensing the solvent which are connected to the container 30. The means for dispensing the solvent comprise, for example, a digital syringe 29. The dispensing means are connected to the control unit which in this instance controls actuation of the digital syringe 29 in accordance with a concentration instruction which the control unit 20 has received and information concerning the quantity of powder which has been supplied to the flask F, which information is supplied by the balance 23.

According to a preferred embodiment, one of the jaws of the second set of pincers 19 comprises a first arm 36 which preferably extends in a direction parallel with the second axis X. The first arm 36 in this instance comprises a cannula 26 and a dispensing pipe which connects the digital syringe 29 to the cannula 26.

In a preferred manner, the workstation further comprises a top dispensing device in order to close the flask F by one of those tops once the desired quantity of powder has been poured into the flask F or once the desired quantity of powder and the desired quantity of solvent have been poured into the flask F.

To this end, the top dispensing device comprises means for introducing tops, which means comprise, for example, a vibrating bowl 31, in which the tops are placed. In a manner known per se, the vibrating bowl 31 allows a single top to be brought to a given position P fixed relative to the workstation.

According to a preferred embodiment, the other of the jaws of the second set of pincers 19 comprises a second arm 37 which preferably extends in the direction in which the first arm 36 extends. The second arm 37 in this instance comprises means for gripping the top which is positioned in a position P in the vibrating bowl 31, the gripping means being at least partially arranged on the second arm 37.

For example, if the tops are composed of elastomer material, the gripping means comprise a rigid suction cup 27 which is arranged on the second arm 37, the suction cup 27 being connected to a pressure reduction generation member such as a vacuum pump 28. The gripping means are connected to the control unit which in this instance controls actuation of the vacuum pump 28.

A work cycle will now be described in accordance with a specific, non-limiting embodiment.

In an initial situation, the flask F is provided on the balance 23. The jaws of the first set of pincers 18 are open and surround the flask F.

The assembly E is in a zero position in which the second set of pincers 19 clamps the cap 2 of the storage reservoir 1 between its jaws, the reservoir 1 not being in a position which is capable of supplying the powder by means of gravitational force. The closure member 8 is mounted on the cap 2 in the closure position.

During a first step, the lifting unit 34 displaces the assembly E as far as a first position in which the assembly E is at a sufficient height to allow the assembly E to be inverted as described in the following paragraph.

During a second step, the rotation unit 33 displaces the assembly E as far as a second position in which the reservoir 1 is inverted so as to be able to supply the powder by means of gravitational force, the reservoir extending in this instance along the axis Z. The closure member 8 is then substantially at the same height as the open end of the flask F, it being possible for an adjustment of the height of the assembly E by the lifting unit 34 to be necessary so that the closure member 8 is substantially at the height of the open end of the flask F.

During a third step, the translation unit 35 displaces the assembly E as far as a third position in which the opening 9 of the closure member 8 is substantially centered about the open end of the flask F.

During a fourth step, the first set of pincers 18 clamps the closure member 8 between the jaws thereof so that the transmitter 21 and the receiver 22 extend at opposite ends of the bore 12.

During a fifth step, in accordance with the instructions from the control unit, the translation unit displaces the second set of pincers 19 and the cap 2 in accordance with the second axis X in order to supply the desired quantity of powder to the flask F. Since the closure member 8 is clamped between the jaws of the first set of pincers 18, the displacements of the second set of pincers 19 and the cap 2 do not affect it.

During a sixth step, once the desired quantity of powder has been supplied to the flask F, the first set of pincers 18 releases the closure member 8 which is then in a closure position.

During a seventh step, the lifting unit 34 displaces the assembly E as far as a fourth position in which the suction cup 27 is at a height greater than the height of a top 32 in a position P of the vibrating bowl.

During an eighth step, the translation unit 25 displaces the assembly E as far as a fifth position in which the suction cup 27 is substantially centered about the top 32. The second set of pincers 19 is formed so that the cannula 26 is then centered about the open end of the flask F.

During a ninth step, the lifting unit 34 displaces the assembly E as far as a sixth position in which the suction cup 27 is substantially resting on the top 32.

During a tenth step, the control unit simultaneously generates an actuation instruction intended for the vacuum pump 28 and a dispensing instruction intended for the digital syringe 29 concerning a quantity of solvent to be dispensed. The suction cup 27 thus grips the top 32 and the digital syringe 29 dispenses a quantity of solvent to the flask F. Preferably, once the digital syringe 29 has dispensed the desired dose of solvent, the control unit compares the signal supplied by the balance 23 to the instruction concerning the quantity of solvent to be dispensed in order to verify whether the instruction has been complied with. It is thereby possible to control the quantity of solvent dispensed more finely than when considering only the indications of the digital syringe 29.

During an eleventh step, the lifting unit 34 displaces the assembly E as far as the fifth position.

During a twelfth step, the translation unit 35 displaces the assembly E as far as a seventh position in which the suction cup 27 is substantially centered about the open end of the flask F so that the top 32 is also centered about that end.

During a thirteenth step, the lifting unit 34 displaces the assembly E as far as an eighth position in which the top 32 is arranged on the free end of the flask F so as to be fitted to the free end.

During a fourteenth step, the control unit generates a stop instruction intended for the vacuum pump 28. The suction cup 27 then releases the top 32.

During a fifteenth step, the assembly E is brought into a zero position by the lifting unit 34, the translation unit 35 and the rotation unit 33.

Naturally, the invention is not limited to the embodiments described and it is possible to apply construction variants thereto without departing from the scope of the invention as defined by the claims.

In particular, although it has been indicated that the powder dispensing device according to the invention was suitable for dispensing quantities of powder in the order of a few tenths of a milligram, the device is also completely suitable for dispensing larger quantities of powder.

Although it has been described that the storage reservoir 1 was a glass vial having a capacity of 4 milliliters, the storage reservoir 1 may be different. For example, the storage reservoir 1 may be an 8-milliliter vial or a 13-milliliter vial.

The cap 2 may cooperate differently with the storage reservoir 1. The cap 2 may, for example, simply be pressed into the neck 4 of the storage reservoir 1.

Although here the relative movement of the closure member 8 and the cap is a translation movement, the device may be arranged so that the closure member 8 (or the cap 2) is displaced in accordance with another movement, for example, in accordance with a rotation movement.

The groove 7 may be a T-like groove and not a groove which is intended for a dovetail type connection. The groove 7 may not comprise any stop studs for the edges 10 of the closure member 8 at each of the ends thereof. For example, the movable plate 16 will then be controlled so as to limit a displacement of the closure member 8 relative to the cap 2.

Although in this instance the flow hole 3 is circular and the opening 9 has a circular cross-section, the hole 3 and the opening 9 may be of different forms. With reference to FIG. 6, the hole 3 is thus of triangular shape and the opening 9 has a circular cross-section. The hole 3 is provided on the cap 2 so that it is one of the tips of the triangle which coincides firstly with the opening 9 of the closure member 8 which allows the start of the flow of the powder to be controlled very finely.

The term "relative displacement means of the cap and the closure member" is intended to be understood to be means which act either on the closure member or on the cap.

By way of a variant, the contactless detection means may be optical means which use a light beam and preferably an infrared beam or ultrasonic means.

Although in this instance the workstation comprises a powder dispensing device according to the second embodiment, the workstation may comprise a powder dispensing device according to the first embodiment. The relative displacement means of the cap and the closure member will then comprise means for displacing the cap relative to the flask and means for displacing the closure member relative to the cap.

The elements of the solvent dispensing devices and top dispensing devices may be different from those described. For example, the first arm may comprise a double cannula, one of the cannulae being connected to the dispensing pipe and the other of the cannulae being connected to means for dispensing inert gas such as argon. In this manner, once the desired quantity of solvent has been supplied to the flask, the control unit will send a signal to the means for dispensing inert gas so that some inert gas is introduced into the flask in order to purge the remaining air in the flask.

The workstation may comprise a different number of devices or different devices from those described in addition to the powder dispensing device. For example, the workstation may comprise only one powder dispensing device or only one powder dispensing device and one solvent dispensing device, or only one powder dispensing device and one top dispensing device. The workstation may comprise only one powder dispensing device and one device comprising means for dispensing inert gas such as argon in order to purge the remaining air in the flask.

The invention claimed is:

1. A powder dispensing device comprising at least one storage reservoir (1) which is provided with a cap (2) comprising a flow hole (3) for the powder, the powder dispensing device further comprising:
a closure member (8) which is provided with an opening (9) and which is mounted so as to be movable relative to the cap between a closure position which prevents a flow of the powder and an open position which allows the flow of the powder through the opening of the closure member, a bore (12) extending through the closure member so as to extend at both sides of the opening of the closure member in a direction which is substantially transverse relative to the flow of the powder;
relative displacement means of the cap and the closure member in order to move the closure member into the two positions thereof, the relative displacement means being connected to a control unit (20) which is connected to contactless detection means of the flow of the powder, the detection means comprising, at a first end of the bore of the closure member, at least one transmitter (21) of a wave in the bore and, at a second end of the bore, at least one receiver (22) for detecting the wave transmitted.

2. The device as claimed in claim 1, wherein the flow hole (3) is circular and, in accordance with a plane of section normal relative to the flow direction of the powder, the opening (9) of the closure member (8) has a circular cross-section.

3. The device as claimed in claim 2, wherein the opening (9) has a circular cross-section which is substantially identical to the flow hole (3) in the region of a face of the closure member (8) which is opposite the cap (2).

4. The device as claimed in claim 1, wherein the closure member (8) is mounted so as to be movable on the cap (2) between the open position and the closure position and is displaced during operation by the relative displacement means between the open and closure positions.

5. The device as claimed in claim 4, wherein the closure member (8) is mounted so as to be movable in translation on the cap (2) in a displacement direction which is transverse relative to the flow direction of the powder.

6. The device as claimed in claim 4, wherein the relative displacement means comprise a set of pincers (15) having parallel jaws, each jaw being intended to cooperate with a lateral face opposite the closure member (8) so as to clamp the closure member between the two jaws.

7. The device as claimed in claim 6, wherein one of the jaws carries the transmitter (21) and the other of the jaws carries the receiver (22), the set of pincers (15) being arranged so that, when the jaws clamp the closure member (8), the transmitter (21) and the receiver (22) extend at the opposite ends of the bore (12).

8. The device as claimed in claim 1, wherein the transmitter (21) and the receiver (22) are carried by the relative displacement means.

9. The device as claimed in claim 1, wherein the cap (2) is mounted so as to be movable on the closure member (8) and is displaced during operation by the relative displacement means in order to bring the closure member into the open position and the closure position.

10. The device as claimed in claim 1, wherein a face of the cap (2) comprising the flow hole (3) comprises a groove (7), the closure (8) having opposite edges (10) which are slidingly engaged in the groove.

11. The device as claimed in claim 1, wherein the bore (12) extends at one side and the other of the opening (9) of the closure member (8) substantially in a displacement direction of the closure member relative to the cap (2).

12. A cap (2) for a device as claimed in claim 1, wherein an internal surface of the cap is tapped in order to cooperate with a threaded external surface of a neck (4) of the reservoir (1).

13. A workstation comprising a powder device, comprising at least one storage reservoir which is provided with a cap comprising a flow hole for the powder, the powder device further comprises:
a closure member provided with an opening and which is mounted so as to be movable relative to the cap between a closure position which prevents a flow of the powder and an open position which allows the flow of the powder through the opening of the closure member, a bore extending through the closure member so as to extend at both sides of the opening of the closure member in a direction which is substantially transverse relative to the flow of the powder;
relative displacement means of the cap and the closure member in order to move the closure member into the two positions thereof, the relative displacement means connected to a control unit which is connected to contactless detection means of the flow of the powder, the detection means comprising, at a first end of the bore of the closure member, at least one transmitter of a wave in the bore and, at a second end of the bore, at least one receiver for detecting the wave transmitted.

14. The workstation as claimed in claim 13, further comprising a solvent dispensing device for dispensing a quantity of solvent, a dispensing tops device for tops for closing a flask which has received powder and solvent, the relative displacement means of the cap and the closure member being arranged in the workstation in order to displace in the workstation at least one assembly formed by the reservoir, the cap and the closure member from one device to another.

15. The workstation as claimed in claim 13, wherein the flow hole is circular and, in accordance with a plane of section normal relative to the flow direction of the powder, the opening of the closure member has a circular cross-section.

16. The workstation as claimed in claim 15, wherein the opening has a circular cross-section which is substantially identical to the flow hole in a region of a face of the closure member which is opposite the cap.

17. The workstation as claimed in claim 13, wherein the closure member is mounted so as to be movable on the cap between the open position and the closure position and is displaced during operation by the relative displacement means between the open and closure positions.

18. The workstation as claimed in claim 17, wherein the closure member is mounted so as to be movable in translation on the cap in a displacement direction which is transverse relative to the flow direction of the powder.

19. The workstation as claimed in claim 17, wherein the relative displacement means comprise a set of pincers having parallel jaws, each jaw being intended to cooperate with a lateral face opposite the closure member so as to clamp the closure member between the two jaws.

20. The workstation as claimed in claim 19, wherein one of the jaws carries the transmitter and the other of the jaws carries the receiver, the set of pincers being arranged so that, when the jaws clamp the closure member, the transmitter and the receiver extend at opposite ends of the bore.

21. The workstation as claimed in claim 13, wherein the transmitter and the receiver are carried by the relative displacement means.

22. The workstation as claimed in claim 13, wherein the cap is mounted so as to be movable on the closure member and is displaced during operation by the relative displacement means in order to bring the closure member into the open position and the closure position.

23. The workstation as claimed in claim 13, wherein a face of the cap comprising the flow hole comprises a groove, the closure having opposite edges which are slidingly engaged in the groove.

24. The workstation as claimed in claim 13, wherein the bore extends at one side and the other of the opening of the closure member substantially in a displacement direction of the closure member relative to the cap.

25. A powder dispensing device comprising at least one storage reservoir which is provided with a cap comprising a flow hole for the powder, the powder dispensing device further comprising:
- a closure member which is provided with an opening and which is mounted so as to be movable relative to the cap between a closure position which prevents a flow of the powder and an open position which allows the flow of the powder through the opening of the closure member, a bore extending through the closure member so as to extend at both sides of the opening of the closure member in a direction which is substantially transverse relative to the flow of the powder;
- relative displacement mover of the cap and the closure member in order to move the closure member into the two positions thereof, the relative displacement mover being connected to a control unit which is connected to a contactless detector of the flow of the powder, the detector of the flow of powder comprising, at a first end of the bore of the closure member, at least one transmitter of a wave in the bore and, at a second end of the bore, at least one receiver for detecting the wave transmitted.

26. A powder dispensing device comprising at least one storage reservoir which is provided with a cap comprising a flow hole for the powder, the powder dispensing device further comprising:
- a closure member which is provided with an opening and which is mounted to a support so as to be movable relative to the cap between a closure position which prevents a flow of the powder and an open position which allows the flow of the powder through the opening of the closure member, a bore extending through the closure member so as to extend at both sides of the opening of the closure member in a direction which is substantially transverse relative to the flow of the powder; and
- a control unit connected to a contactless detector of the flow of the powder, the detector of the flow of powder comprising, at a first end of the bore of the closure member, at least one transmitter of a wave in the bore and, at a second end of the bore, at least one receiver for detecting the wave transmitted.

* * * * *